United States Patent [19]

Suzuki

[11] Patent Number: 5,093,116
[45] Date of Patent: Mar. 3, 1992

[54] METHOD OF TREATING VIRAL INFECTION UTILIZING INTEFERON α AND PIPYRIDAMOLE

[75] Inventor: Nobuo Suzuki, Funabashi, Japan

[73] Assignee: Boehringer Ingelheim Int. GmbH, Ingelheim am Rhein, Fed. Rep. of Germany

[21] Appl. No.: 360,304

[22] Filed: Jun. 2, 1989

[30] Foreign Application Priority Data

Jun. 2, 1988 [GB] United Kingdom ............... 8813032

[51] Int. Cl.$^5$ ...................... A61K 37/66; A01N 43/54
[52] U.S. Cl. .................................. 424/85.7; 514/258; 514/889
[58] Field of Search ................ 424/85.7; 514/258, 889

[56] References Cited

U.S. PATENT DOCUMENTS

| | | | |
|---|---|---|---|
| 3,031,450 | 4/1962 | Fischer et al. | 260/247.5 |
| 4,258,061 | 3/1981 | Cronin et al. | 424/325 |
| 4,283,393 | 8/1981 | Field et al. | 424/180 |
| 4,461,757 | 7/1984 | Ogilvie | 424/85 |
| 4,462,986 | 7/1984 | Smith | 424/85 |
| 4,491,583 | 1/1985 | Cronin et al. | 424/250 |
| 4,499,093 | 2/1985 | Galabov et al. | 514/258 |
| 4,636,383 | 1/1987 | Nagahuhan | 424/85 |
| 4,824,674 | 4/1989 | Becker | 424/427 |
| 4,957,733 | 9/1990 | Cole et al. | 424/85.4 |

FOREIGN PATENT DOCUMENTS

| | | |
|---|---|---|
| 32562 | 1/1980 | European Pat. Off. . |
| 32134 | 7/1981 | European Pat. Off. . |
| 68191 | 6/1982 | European Pat. Off. . |
| 115613 | 12/1982 | European Pat. Off. . |
| 109234 | 5/1984 | European Pat. Off. . |
| 0295317 | 6/1987 | European Pat. Off. . |
| 2025227 | 7/1979 | United Kingdom . |
| WO86/03412 | 6/1986 | United Kingdom . |

OTHER PUBLICATIONS

Partial European Search Report.
*The Biology of the Interferon System*, Elsevier/North Holland Biomedical Press E. DeMaeyer et al., eds., pp. 323–380 (1981).
Sundmacher et al., *Lancet II*, p. 687 (1978).
Tonew, M. et al., *Acta Virol.* (*Engl. Ed.*) 21:146–150 (1977).
Tonew, M. et al., *Acta Virol.* (*Engl. Ed.*) 22:287–295 (1978).
Zopel. P., *Z. Allg. Mikrobiol.* 22(9):661–670 (1982).
Kozhukharova, M.S. et al., *Vopr. Virusol.* 32(3):294–297 (1987).
Kuzmov, K. et al., *Zh. Mikrobiol. Epidemiol. Immunobiol.* 6:26–30 (1985).

*Primary Examiner*—Leonard Schenkman
*Assistant Examiner*—T. J. Criares
*Attorney, Agent, or Firm*—Sterne, Kessler, Goldstein & Fox

[57] ABSTRACT

A method of enhancing the antiviral activity of IFN-α and especially human IFN-α is disclosed which comprises administration of Dipyridamole or a pharmaceutically acceptable salt thereof to a subject receiving IFN-α. Also disclosed are pharmaceutical compositions comprises of IFN-α and dipyridamole or a pharmaceutically acceptable salt thereof.

13 Claims, 3 Drawing Sheets

METHOD OF TREATING VIRAL INFECTION UTILIZING INTEFERON α AND PIPYRIDAMOLE

FIELD OF THE INVENTION

The present invention relates generally to the treatment of viral infection, in particular, the treatment of viral infections using IFN-α. More specifically the invention relates to the use of dipyridamole for enhancing the antiviral activity of IFN-α, a method of treating a human or animal suffering from a viral infection by combined therapy with dipyridamole and IFN-α, the use of dipyridamole and IFN-α for preparing pharmaceutical preparations for treating such viral infection and to pharmaceutical preparations so produced.

BACKGROUND OF THE INVENTION

Human interferon (HuIFN-α) is known to be useful in the treatment of certain forms of tumors, e.g. hairy cell leukemia.

HuIFN-α has also been recognized for some time as a potentially valuable drug for the treatment of some virus infections (see e.g. *The Biology of the Interferon System*, Elsevier/North Holland Biomedical Press 323–380 (1981)). HuIFN-α has been reported for instance as being effective in the treatment of ocular Herpes Simplex, when applied at high dosages together with Trifluorothymidin (Sundmacher et al., *Lancet II* 687: (1978)).

The compound 2,6-bis (diethanolamine)-4, 8-dipiperidino-pyrimido [5,4-d]pyrimidine, which has the generic name dipyridamole, and its preparations have been described in, for example, U.S. Pat. No. 3,031,450. Dipyridamole is a well known vasodilator and also has platelet aggregation inhibiting properties; in view of these properties it has found widespread use for many years in the treatment of chronic coronary insufficiency and in the prophylaxis and treatment of heart infarcts as well as in the prophylaxis of arterial thrombosis.

Antiviral activity for dipyridamole has been reported. For instance, in East German Patent No. 116,752 (C.A. 85; 37239r) compositions containing dipyridamole for the prophylactic and therapeutic treatment of virus diseases in humans and animals are described. In *Acta Virol.* (Engl. Ed.), 21(2):146–150 (1977), it is described that when tested in chick embryo, human diploid and FL cell cultures, dipyridamole inhibited D such as vaccinia and pseudorabies virus and those of the Chlamydial family and RNA viruses belonging to Picornaviridal, Togaviridal, Orthmyxoviridal and Paramyxoviridal but that Adenoviruses 1 and 3 were resistant to the compound. In a further publication (*Acta Virol.* [Engl. Ed.] 22(4):287–295 (1978)) various derivatives of dipyrid found to be active against a variety of virus such as Coxsaki BI virus, fowl plague virus, vaccinia and pseudorabies virus. The publication *Z. Allg. Mikrobiol.* 22(9):61–670 (1982), describes work carried out on the in vitro effect of dipyridamole on pseudorabies virus in which it is stated that the antiviral activity of dipyridamole may be due to blocking of the synthesis or the incorporation of infectious viral DNA into the virus core.

A number of authors have reported the induction of interferon using dipyridamole. Thus in *Vopr. Virusol*, 32(3):294–297 (1987), the use of dipyridamole as an agent for preventing acute respiratory viral disease was evaluated. Dipyridamole is described in this article as an interferon inducer. Also in *Zh. Mikrobiol. Epidemiol. Immunobiol.* (6):26–30 (1985), is described a report on the "epidemiological effectiveness of dipyridamole, an interferon-inducing agent used for the prevention of influenza and viral acute respiratory diseases." The report claims a pronounced epidemiological effectiveness of dipyridamole.

No authors have reported or suggested the combined uses of dipyridamole and IFN-α in the treatment of, or prophylaxis of, viral infections, or suggested that any worthwhile results could be expected from such a combined therapy.

SUMMARY OF THE INVENTION

Figure 1:
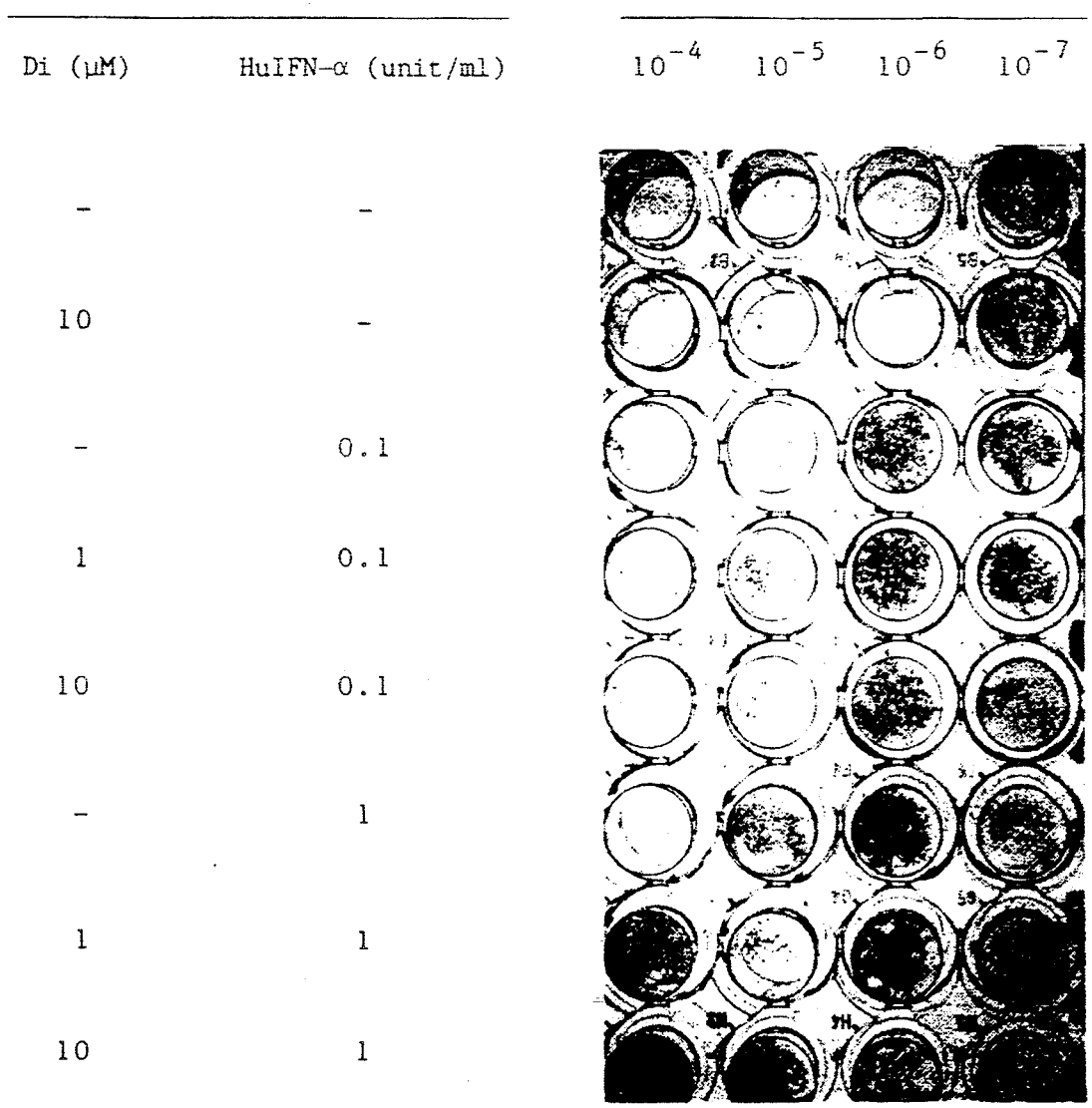
FIG. 1 illustrates the cytopathogenic effect of vesicular stomatitis virus (VSV) in a yield reduction assay in $UV^r$-1 cells. Di, dipyridamole. The pretreatment conditions are shown to the left of the assay plate.
Figure 2:
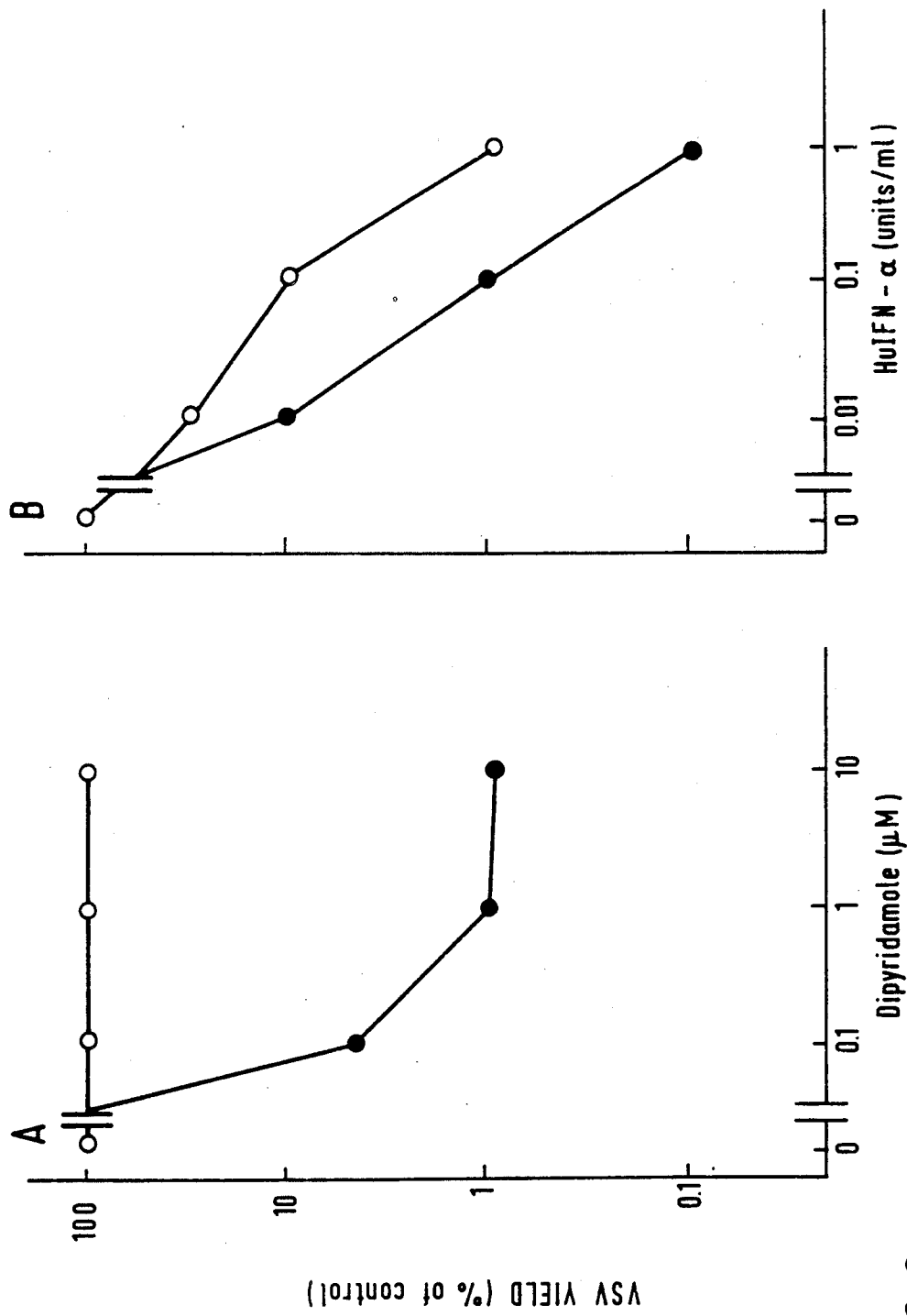
FIG. 2 graphically illustrates the VSV produced in RSa cells pretreated with HuIFN-α and dipyridamole before infection. The VSV yield in control RSa cells without pretreatment with these agents was 6.5 (log $TCID_{50}$/0.2 ml). A: dipyridamole alone, open circles; dipyridamole plus 0.1 unit.ml HuIFN-α, closed circles. B: HuIFN-α alone, open circles; HuIFN-α plus 1 μM dipyridamole, closed circles.
Figure 3:
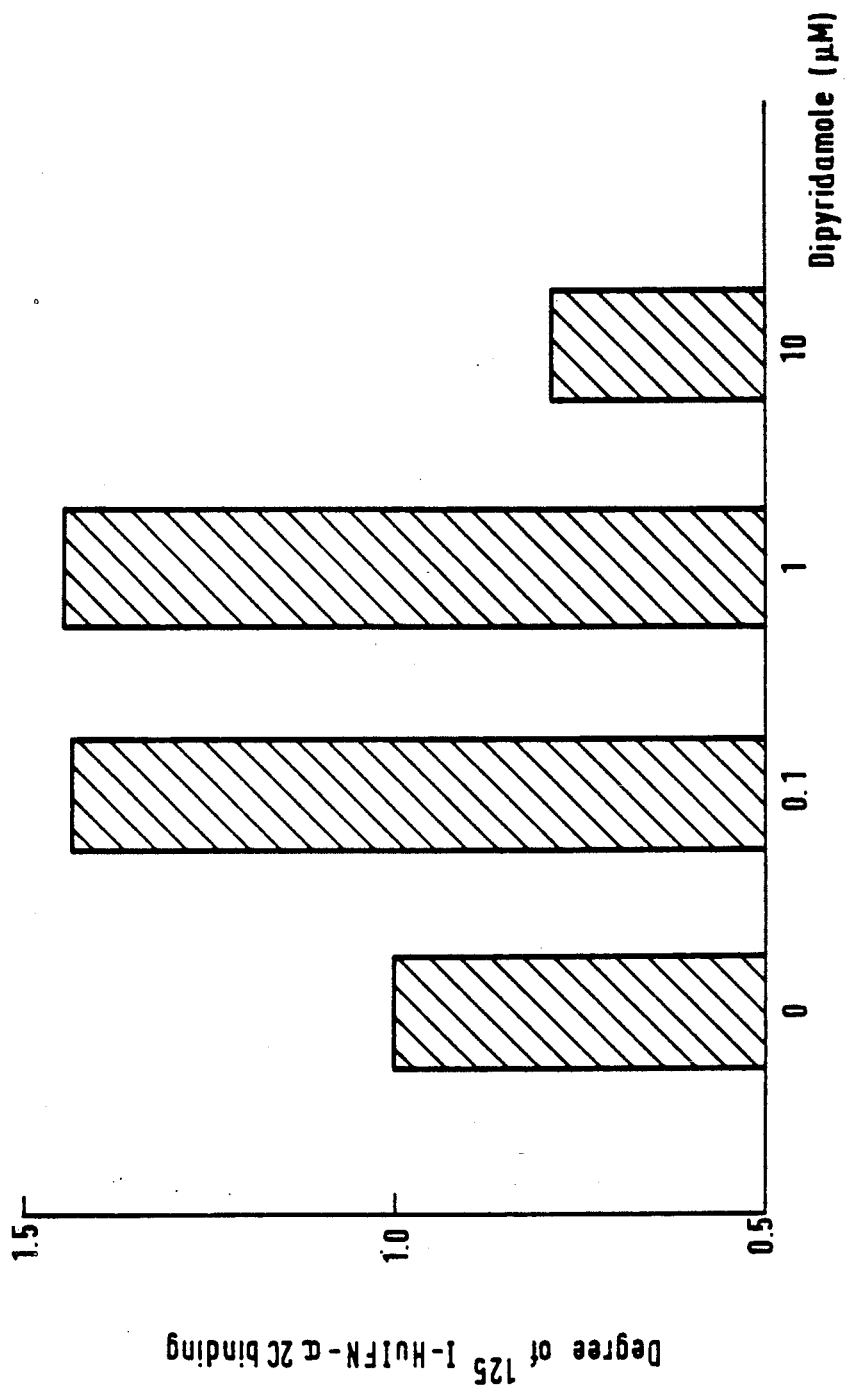
FIG. 3 is a graphical representation of the effect of dipyridamole on binding of $^{125}$I-HuIFN-$α_{2c}$ (5,000 units/ml) to RSa cells. Cells were exposed to agents in combination for 30 min., washed and then the radioactivity of cells was counted by a gamma counter.

Surprisingly, the present inventors now have found that dipyridamole itself, while having in fact no or negligible antiviral activity, is capable of remarkably enhancing the antiviral activity of IFN-α, especially HuIFN-α.

Broadly speaking, the present invention comprises dipyridamole for use in the preparation of a pharmaceutical composition for enhancing the antiviral effects of IFN-α.

A further aspect of the invention comprises a method of treatment or prophylaxis of viral infection of a mammal which comprises administering IFN-α, and dipyridamole or a pharmaceutically acceptable salt thereof, to said mammal, the dipyridamole or salt being administered in an amount such that it enhances the antiviral effect of the IFN-α.

Another aspect of the invention comprises the treatment or prophylaxis of a viral infection of a mammal which comprises administering to the said mammal dipyridamole or a pharmaceutically acceptable salt thereof in an amount sufficient to enhance the antiviral activity of an IFN-α also administered to the mammal.

Yet a further aspect of the invention comprises dipyridamole or a pharmaceutically acceptable salt thereof for use in the manufacture of a pharmaceutical composition suitable for enhancing the antiviral effect of IFN-α when administered to a mammal requiring antiviral treatment and to whom said IFN-α is also administered.

Yet a further aspect of the present invention comprises an IFN-α for use in the manufacture of a pharmaceutical composition for use together with dipyridamole or a pharmaceutically acceptable salt thereof in the treatment or prophylaxis of viral infection of a mammal.

Another aspect of the invention comprises a pharmaceutical composition containing IFN-α and dipyridamole or a pharmaceutically acceptable salt thereof together with conventional pharmaceutical excipients for use in the treatment or prophylaxis of viral infection.

DETAILED DESCRIPTION OF THE INVENTION

The term IFN-α as used herein includes both human and non-human IFN-α depending on whether therapy or prophylaxis on human or non-human mammals is required.

The term HuIFN-α, as used herein includes all HuIFN-αs which have antiviral activity.

The amino acid sequences of various IFN-α's, their preparation by recombinant technology and the preparation of pharmaceutical compositions containing them are described in the literature.

For example, the amino acid sequence and recombinant preparation of HuIFN-$α_{2a}$ is described in European Patent Publication No. 43,980; for HuIFN-$α_{2b}$ these are described in European Patent Publication No. 32,134; and for HuIFN-$α_{2c}$ they are described in European Patent Publication 115,613.

The dipyridamole or salt thereof and interferon should be administered such that they are simultaneously present in the body. Preferably, therefore, they are administered simultaneously or substantially simultaneously. By "substantially simultaneously" is meant that the dipyridamole or salt thereof and interferon are administered at a time(s) such that both substances can interact together in a manner which enhances the antiviral activity of the interferon.

By "pharmaceutically acceptable salt" is intended a salt formed from pharmaceutically acceptable acids or bases, for example, acids such as sulfuric, hydrochloric, nitric, phosphoric, etc., or bases such as alkali or alkaline earth metal hydroxides, ammonium hydroxides, alkyl ammonium hydroxides, etc.

By "subject" is intended an animal in which IFN-α is capable of anti-viral activity.

It is presently considered that the preferred dosages of interferon and dipyridamole for effective antiviral treatment or prophylaxis in humans are those which provide blood levels of at least 0.1 μM, for example, 0.1 to 5 μM dipyridamole, more preferably 0.75 to 1.5 μM and most preferably about 1 μM, and more than 0.01 IU/ml HuIFN-α.

It will be clear that actual dosages may be altered by the attending physician depending upon the circumstances and conditions of the individual patient.

For the use in the practice of the present invention the interferon may be administered by the parenteral route. The dosage and dosage rates are preferably about $2 \times 10^3$ to $20 \times 10^6$ I.U., for example, $2 \times 10^5$ to $4 \times 10^6$ I.U. given twice daily in the case of intravenous administration and once daily in the case of intramuscular injection.

The preparation of suitable dosage forms for IFN-α is well known.

To produce a convenient dosage form for parenteral use an appropriate amount of the HuIFN-α may be dissolved in 5% human serum albumin, if necessary containing a suitable buffer solution. This resulting solution is then passed through a bacteriological filter and the filtered solution is distributed between vials under aseptic conditions, each vial containing an appropriate amount of the interferon and, if desired, lyophilized.

The glass vials are preferably stored under cool conditions (−20° C.) before use. The interferon may be formulated in known manner in order to obtain pharmaceutically usable compositions, the interferon being mixed with a pharmaceutically acceptable carrier substance: conventional carriers and their formulation are described by E. W. Martin in *Remington's Pharmaceutical Sciences,* Mack Publishing Co., Easton, Pa., to which referenced is expressly made.

The dipyridamole or salt thereof can be administered by any of the usual routes of administration, for example orally or parenterally. At present the preferred route of administration is oral. The recommended dosages are 25 to 200 mg. for example, 75 to 100 mg four times daily for tablets and dragees or 150 to 200 mg twice daily for delayed release forms. By the intravenous route the dipyridamole can be given, for example, by continuous infusion of 3 mg/kg per day.

Dipyridamole is commercially available under the Trade Mark Persantin in a number of forms, for instance injection solution containing 10 mg dipyridamole and dragees containing 25 mg and 75 mg dipyridamole are described in the Rote Liste 1987 published by the Bundesverband der Pharmazeutischen Industrie e.V., D-6000 Frankfurt a.M., West Germany. Suitable dosage forms containing various amounts of dipyridamole can be prepared using standard techniques. In addition a number of special galenic forms have been described in the literature which are aimed at providing either accelerated or delayed (sustained) release and resorption of dipyridamole, for instance the retard capsule form described in European Patent Publication No. 32,562; and the instant release form described in European Patent Publication No. 68,191. A further delayed release galenic form is described in British Patent No. 2,025,227.

Having now generally described this invention, the same will become more readily understood by reference to specific examples included herein for purposes of illustration only, and not intended to be limiting unless otherwise specified.

EXAMPLE 1

Enhancement of Antiviral Activity of HuIFN-α By Dipyridamole

The present invention is predicated on the observation that dipyridamole demonstrated the surprising property of enhancing the antiviral activity of human IFN-α on a virus strain. Thus a test was carried out as described below:

Natural HuIFN-$α_{2c}$ and $^{125}$I labelled HuIFN-$_{2c}$ preparations; ($10^8$ international reference units (I.U.)/mg protein), were obtained from Dr. Karl Thomas GmbH, West Germany. Dipyridamole was provided by Boehringer Ingelheim GmbH (W-Germany). Other chemical agents were purchased from Nakarai Co. Ltd., Japan.

The antiviral action was measured in a yield reduction assay with a strain of the Indiana serotype of vesicular stomatitis virus (VSV) as described in Suzuki et al.. *Mutation Research* 106:357–376 (1982). Samples of VSV, produced in human RSa cells with and without pretreatment for 24 hours by dipyridamole and HuIFN-α before virus challenge, were applied to cells of a UV$^r$-1 strain. UV$^r$-1, which is a variant strain for RSa, has an increased resistance to the cell proliferation inhibition effect of interferon but the usual suspectibility of cytopathogenic effect (CPE) of VSV (Suzuki et al.. *J. Gen. Virol.* 67:651–661 (1986). Thus, the effect of HuIFN-α and dipyridamole on virus production could be measured by CPE of VSV in UV$^r$-1 cells in proportion to the production levels without anti-cellular effects being caused by the agents which may remain in the VSV-samples obtained.

As shown in FIG. 1, CPE was reduced in samples obtained from RSa cells pretreated with dipyridamole and HuIFN-α before VSV infection, although the CPE from pretreatment with dipyridamole alone was much the same as that from non-pretreatment. The appropriate concentration of dipyridamole for the enhancement of HuIFN-α activity was more than 0.1 μM as shown in FIG. 2A. Even if the number of units of HuIFN-α was increased, the enhancement by dipyridamole appeared constant (about ten times the antiviral activity of HuIFN-α alone), as shown in FIG. 2B. The mechanism of the enhancement of antiviral activity of HuIFN-α by dipyridamole has not been elucidated unequivocally yet, but, we have found that dipyridamole enhances HuIFN-α binding capacity. A binding assay was performed as described in Suzuki et al. *Supra* (1986). As shown in FIG. 3, 0.1 μM-1 μM dipyridamole enhances the binding capacity in RSa cells to about 1.5 times that in cells non-treated with dipyridamole.

The results presented here are the first which show the surprising effect of dipyridamole on the antiviral action of IFN-α.

EXAMPLES 2-13

Examples of Pharmaceutical Compositions

Example 2: Lyophilized Preparation Containing 0.04 mg I.U. Recombinant HuIFN$\alpha_{2c}$ (rHuIFN-$\alpha_{2c}$)

| Composition: | | |
|---|---|---|
| (1) | rHuIFN-$\alpha_{2c}$ | 0.04 mg ($4 \times 10^6$ I.U.); |
| (2) | Isotonic phosphate buffer pH7 | q.s.; |
| (3) | Human serum albumin | 20.0 mg; and |
| (4) | Water for injection | 1.0 ml. |

Preparation:

The additives (2) and (3) are dissolved in ⅔ of the total required amount of water. The exact amount of HuIFN-$\alpha_{2c}$ is then added and the solution is brought to the final required volume by adding the remaining water, filtered through 0.22 μM filter and filled into vials, lyophilized and stoppered.

EXAMPLES 3 TO 5

Using a process analogous to Example 2 lyophilized preparations containing the following amounts of rHUIFN-$\alpha_{2c}$ in I.U. were prepared:

(3) $2 \times 10^3$ (Example 3)

(4) $2 \times 10^5$ (Example 4)

(5) $20 \times 10^6$ (Example 5).

EXAMPLE 6

Examples 2 to 5 were repeated using rHUIFN-$\alpha_{2a}$ and HuIFN-$\alpha_{2b}$.

EXAMPLE 7

Lyophilized preparation containing $2 \times 10^3$-$20 \times 10^6$ I.U. rHuIFN-$\alpha_2$

| Composition: | | |
|---|---|---|
| (1) | IFN-$\alpha_2$ | $2 \times 10^3 - 20 \times 10^6$ I.U.; |
| (2) | KCl | 0.2 mg; |
| (3) | $Na_2PHO_4 \cdot 12H_2O$ | 2.9 mg; |
| (4) | $KH_2PO_4$ | 0.2 mg; |
| (5) | NaCl | 8.0 mg; |
| (6) | Human serum albumin | 20.0 mg; and |
| (7) | Water for injection | 1.0 ml. |

Preparation:

The buffer materials (2), (3), (4), the stabilizer (6), the sodium chloride (5) and the active ingredient (1) were dissolved in the water (7). After sterile filtration the solution was filled into vials under sterile conditions and freeze dried.

EXAMPLE 8

Example 7 was repeated using rHuIFN-$\alpha_{2a}$ and rHuIFN-$\alpha_{2b}$.

EXAMPLE 9

A dragee containing 75 mg dipyridamole

| Composition: | | |
|---|---|---|
| (1) | dipyridamole | 7.5 kg; |
| (2) | lactose | 4.2 kg; |
| (3) | maize starch | 2.4 kg; |
| (4) | polyvinylpyrolidine | 0.7 kg; and |
| (5) | magnesium stearate | 0.2 kg. |

Preparation:

(1)+(2)+(3)+(4) were mixed and to the mixture was added water to form a moist mass.

The moist mass was passed through a sieve having 1.2 mm spacing and dried at 45° C. in a drying chamber. The dry granules were passed through a sieve having 1 mm spacing and mixed with (5).

The final mixture was pressed to form dragees with a core weight of 150 mg. The dragee cores so formed were covered by a surface coating in known manner, the coating consisting essentially of sugar and talc. This coating may also contain permitted coloring agents. The finished dragees are polished with wax. The dragee weight was 200 mg.

EXAMPLE 10

An ampoule containing 10 mg dipyridamole

| Composition: | | |
|---|---|---|
| (1) | dipyridamole | 10 mg; |
| (2) | tartaric acid | 4 mg; |
| (3) | polyethylene glycol | 100 mg; |
| (4) | Hydrochloric acid (IN) to adjust to pH 2.7 | q.s. (~0.018 m); and |
| (5) | Water for injection add. | 2 ml. |

Preparation:

The dipyridamole and other ingredients were dissolved in water. After sterile filtration the solution is filled into ampoules and sterilized by heating.

EXAMPLE 11

An ampoule from Examples 2 to 8 is formulated for injection using water for injection or isotonic saline solution to provide an injection solution of 2 ml.

EXAMPLE 12

Combination preparation containing dipyridamole and HuIFN-α

The contents of the ampoules from Examples 2 to 8 were reconstituted with the contents of the dipyridamole ampoule from Example 10.

The combination preparation of HuIFN-$\alpha_2$ with dipyridamole was stable at room temperature for about 6 hours.

EXAMPLE 13

Capsules containing delayed-release dipyridamole formations

Thirty kg of rounded tartaric acid starter pellets is sprayed, in a special pan, with a suspension consisting of isopropanol, dipyridamole and polyvinylpyrrolidone until the resulting pellets of active substance contain about 45% dipyridamole.

These pellets are sprayed with a lacquer consisting of methacrylic acid/methyl methacrylate copolymer (brand name Eudragit S) and hydroxypropylmethylcellulose phthalate (brand name HP 55) in a weight ratio 85:15 to 50:50.

The organic lacquer solution also contains plasticizer and talc. Two pellet components are sprayed with 5% and 7% of coating and different ratios of lacquer components within the limits specified and are mixed together.

In a special capsule making machine, the quantity of pellets corresponding to 150-200 mg of dipyridamole are packed into an appropriate sized capsules.

It is understood that these descriptions, examples and embodiments are for illustrative purposes only, and that various modifications would be suggested within the spirit and purview of this application and the scope of the appended claims.

What is claimed is:

1. A method of treating a viral infection in a mammal wherein said viral infection is capable of being treated with IFN-α which method comprises substantially simultaneous administration of IFN-α and dipyridamole or a pharmaceutically acceptable salt thereof to a mammal in need of said administration, wherein said dipyridamole or salt thereof is administered in an an effective amount such that said dipyridamole or said pharmaceutically acceptable salt thereof enhances the antiviral effect of the interferon.

2. A method for enhancing the antiviral effect of IRN-α in a subject being administered IFN-α which comprises substantially simultaneous administration of IFN-α and dipyridamole in a pharmaceutically acceptable salt thereof to a subject in need of said administration in an effective amount sufficient to enhance the antiviral activity of IFN-α.

3. The method of any one of claim 1 or claim 2, wherein said IFN-α is administered simultaneously with said dipyridamole or said pharmaceutically acceptable salt thereof.

4. The method of any one of claim 1 or claim 2, wherein said IFN-α is administered essentially simultaneously with said dipyridamole or said pharmaceutically acceptable salt thereof.

5. The method of and one of claim 1 or claim 2, wherein said dipyridamole is administered orally.

6. The method of claim 5, wherein said dipyridamole is administered at doses of 25-200 mg daily.

7. The method of any one of claim 1 or claim 2, wherein said dipyridamole is administered parenterally.

8. The method of claim 7, wherein said parenteral administration is by intravenous administration.

9. The method of claim 8, wherein said intravenous administration of dipyridamole infuses 3 mg/kg body weight/day.

10. The method of any one of claim 1 or 2, wherein said dipyridamole is in an accelerated release form.

11. The method of any one of claim 1 or 2, wherein said dipyridamole is in a delayed release form.

12. The method of any of claim 1 or 2, wherein said interferon is recombinant interferon.

13. The method of any one of claims 1 or 2, wherein said IFN-α is IFN-$\alpha_{2c}$.

* * * * *

UNITED STATES PATENT AND TRADEMARK OFFICE
CERTIFICATE OF CORRECTION

PATENT NO. : 5,093,116

DATED : March 3, 1992

INVENTOR(S) : Nobuo Suzuki

Page 1 of 2

It is certified that error appears in the above-identified patent and that said Letters Patent is hereby corrected as shown below:

On the title page, in items [54] and [56]:
In the title: "INTEFERON" should read --INTERFERON-- and "PIPYRIDAMOLE" should read "DIPYRIDAMOLE".

In the Foreign Application Priority Data: "8813032" should be --8813032.3--.

In the References Cited, under Foreign Patent Documents: Please add --116752, 12/75, East Germany (DD)--; and also add --43980, 01/82, European Pat. Off.--.

| Column | Line | |
|---|---|---|
| 1 | 18 | "Human interferon (HuIFN-$\alpha$)" should read --Human interferon-$\alpha$ (HuIFN-$\alpha$)--. |
| | 47 | "D" should read --DNA viruses--. |
| | 54 | "dipyrid" should read --dipyridamole--. |

UNITED STATES PATENT AND TRADEMARK OFFICE
CERTIFICATE OF CORRECTION

PATENT NO. : 5,093,116
DATED : March 3, 1992
INVENTOR(S) : Nobuo Suzuki

It is certified that error appears in the above-identified patent and that said Letters Patent is hereby corrected as shown below:

| Column | Line | |
|---|---|---|
| 8 | 3 | "in an an effective" should read --in an effective--. |
| | 8 | "IRN-α" should read --IFN-α--. |
| | 10 | "in a pharmaceutically" should read --or a pharmaceutically--. |

Signed and Sealed this

Nineteenth Day of July, 1994

Attest:

BRUCE LEHMAN

Attesting Officer

Commissioner of Patents and Trademarks